(12) United States Patent
Ogata

(10) Patent No.: US 9,379,412 B2
(45) Date of Patent: Jun. 28, 2016

(54) IONIC COMPOUND, METHOD FOR PRODUCING THE SAME, AND ION CONDUCTIVE MATERIAL

(75) Inventor: Shin-ichi Ogata, Nagakute (JP)

(73) Assignee: KABUSHIKI KAISHA TOYOTA CHUO KENKYUSHO, Nakagute-shi (JP)

( * ) Notice: Subject to any disclaimer, the term of this patent is extended or adjusted under 35 U.S.C. 154(b) by 326 days.

(21) Appl. No.: 13/817,337

(22) PCT Filed: Sep. 21, 2011

(86) PCT No.: PCT/JP2011/072301
§ 371 (c)(1),
(2), (4) Date: Feb. 15, 2013

(87) PCT Pub. No.: WO2012/039509
PCT Pub. Date: Mar. 29, 2012

(65) Prior Publication Data
US 2013/0143779 A1 Jun. 6, 2013

(30) Foreign Application Priority Data
Sep. 22, 2010 (JP) ................. 2010-212245

(51) Int. Cl.
*C07F 5/04* (2006.01)
*C07F 5/06* (2006.01)
(Continued)

(52) U.S. Cl.
CPC ............ *H01M 10/056* (2013.01); *C07C 43/11* (2013.01); *C07F 5/04* (2013.01); *C07F 5/069* (2013.01);
(Continued)

(58) Field of Classification Search
CPC .................................. C07F 5/04; C07F 5/069
USPC .............................. 508/200; 44/365; 556/182
See application file for complete search history.

(56) References Cited

U.S. PATENT DOCUMENTS

2003/0108798 A1   6/2003   Fujinami

FOREIGN PATENT DOCUMENTS

EP      2 062 902 A1    5/2009
JP      A-08-301879     11/1996
(Continued)

OTHER PUBLICATIONS

Aug. 27, 2012 International Search Report issued in International Application No. PCT/JP2011/072301.
(Continued)

*Primary Examiner* — Prem C Singh
*Assistant Examiner* — Frank C Campanell
(74) *Attorney, Agent, or Firm* — Oliff PLC

(57) ABSTRACT

An ionic compound is represented by formula (1): $AM(OY^1)(OY^2)(OY^3)(OY^4)$. A is a group 1 element. M is a group 13 element. $Y^1$ is one selected from an oligoalkylene ether group, an oligoalkylene thioether group, and an oligoalkylene amino group and includes an electron donating group on carbon that is located in one of $\alpha$-$\gamma$ positions with respect to oxygen atom adjacent to M. $Y^2$, $Y^3$, and $Y^4$ are the same each other or different from each other or cross-linked to each other. $Y^2$, $Y^3$, and $Y^4$ are each any one of an alkyl group, an alkyl group with a fluorinated terminal, an aryl group, and one selected from the group consisting of an oligoalkylene ether group, an oligoalkylene thioether group, and an oligoalkylene amino group and including an electron donating group on carbon that is located in one of $\alpha$-$\gamma$ positions with respect to oxygen atom adjacent to M.

8 Claims, 6 Drawing Sheets

(51) Int. Cl.
  *C10L 1/24* (2006.01)
  *H01M 10/056* (2010.01)
  *C07C 43/11* (2006.01)
  *C08G 65/22* (2006.01)
  *C08G 65/328* (2006.01)
  *C08G 75/02* (2016.01)
  *H01M 10/0568* (2010.01)
  *H01M 10/0525* (2010.01)
  *C08G 65/322* (2006.01)
  *C08L 71/02* (2006.01)

(52) U.S. Cl.
  CPC .............. *C08G 65/22* (2013.01); *C08G 65/322* (2013.01); *C08G 65/328* (2013.01); *C08G 75/02* (2013.01); *C08L 71/02* (2013.01); *H01M 10/0525* (2013.01); *H01M 10/0568* (2013.01)

(56) References Cited

FOREIGN PATENT DOCUMENTS

| | | |
|---|---|---|
| JP | A-2003-146941 | 5/2003 |
| JP | A-2004-067554 | 3/2004 |
| JP | A-2004-307481 | 11/2004 |
| JP | A-2007-099705 | 4/2007 |
| JP | A-2007-099706 | 4/2007 |
| JP | A-2007-115527 | 5/2007 |
| JP | A-2008-069102 | 3/2008 |
| WO | WO 96/38872 A1 | 12/1996 |

OTHER PUBLICATIONS

Aug. 27, 2012 Written Opinion issued in International Application No. PCT/JP2011/072301.

IONIC COMPOUND, METHOD FOR PRODUCING THE SAME, AND ION CONDUCTIVE MATERIAL

TECHNICAL FIELD

The present invention relates to an ionic compound, a method for producing the same, and an ion conductive material.

BACKGROUND ART

Conventionally, an ionic liquid is known as an ionic compound. The ionic liquid receives attention as a material facilitating development of a capacitor, a lithium ion battery, a fuel cell, a solar cell, and the like. The ionic liquid has low environmental load and high heat-resistance and is expected as solvents for metal plating and various reaction solvents. Further, the ionic liquid is being studied for use as a lubricant in special environments such as space development field and possibilities of using the ionic liquid are expected in many fields.

When using the ionic liquid as a solvent of a lithium ion battery, the ionic liquid is superior in terms of safety to an organic solvent such as a carbonate solvent because it does not ignite due to its nonvolatility. However, a lithium salt is dissolved in the ionic liquid for the lithium ion battery. Thus, 2 (two) cations and 2 (two) anions present in the solution and interfere with the lithium ion transfer. Taking this into consideration, polyethylene glycol (PEG) based ionic compounds including the lithium ion as the cation has been developed.

Patent document 1 discloses $LiAl[O(CH_2CH_2O)_3CH_3]_4$ that is a colorless liquid and has an ionic conductance of $1.1 \times 10^{-5}$ S/cm (25° C.). Patent document 2 notes an introduction of an electron withdrawing group into the PEG based ionic compound, that decreases a charge density of the anion so as to reduce an anion-cation interaction, and discloses a production example of $LiAl[O(CH_2CH_2O)_mCH_3]_2$ $[OCOCF_3]_2$ (m=3, 7.2, 11.8). In the patent document 2, LiAl $[O(CH_2CH_2O)_mCH_3]_2[OCOOF_3]_2$ is in a solid state when m=3, and in a liquid state when m=7.2 or 11.8. The patent document 2 discloses that the ionic conductance of $LiAl[O(CH_2CH_2O)_mCH_3]_2[OCOCF_3]_2$ is highest when m=7.2. Further, patent document 3 discloses that the ionic conductance is favorably improved by adding Lewis acid to the PEG based ionic compound into which the electron withdrawing group is introduced. In addition, patent documents 4-8 also disclose PEG based ionic compounds.

Patent Document 1: Japanese Patent Laid-Open No. H8-301879
Patent Document 2: JP 2003-146941 A
Patent Document 3: JP 2007-115527 A
Patent Document 4: JP 2007-99706 A
Patent Document 5: JP 2007-99705 A
Patent Document 6: JP 2008-69102 A
Patent Document 7: JP 2004-307481 A
Patent Document 8: JP 2004-67554 A

DISCLOSURE OF THE INVENTION

Patent document 2 discloses that the ionic conductance changes in accordance with a repeating number n of —$CH_2CH_2O$— of PEG chain when the electron withdrawing group is introduced into the PEG based ionic compound so as to reduce the anion-cation interaction. Concretely, the ionic conductance becomes highest when m=7.2 and becomes second highest when n=11.8 in comparing between the cases of n=3, 7.2, and 11.8 (refer to FIG. 1 of Patent Document 2).

However, a density of the lithium ion or a carrier ion unfavorably decreases because the ratio of —$CH_2CH_2O$— to Li increases when n=7, 2 or 11.8. Thus, it is desired to develop a compound having both a small repeating number and an excellent ionic conductance.

The present invention is made to solve the above problem and provides an ionic compound including a shorter oligoether group and having excellent characteristics (such as an ionic conductance).

In order to solve the above problem, the present inventors found that an ionic compound having a small repeating number of alkylene ether and excellent characteristics was obtained by an introduction of alkyl as an electron donating group into the oligoalkylene ether group bonded to Al in PEG based ionic compound including a Al ate complex. This finding led to the realization of the present invention.

More particularly, an ionic compound of the present invention is represented by the formula (1): $AM(OY^1)(OY^2)(OY^3)(OY^4)$. In the ionic compound, A is a group 1 element; M is a group 13 element; $Y^1$ is one selected from the group consisting of an oligoalkylene ether group, an oligoalkylene thioether group, and an oligoalkylene amino group and includes an electron donating group on carbon that is located in one of α-γ positions with respect to oxygen atom adjacent to M; $Y^2$, $Y^3$, and $Y^4$ are the same each other or different from each other or cross-linked each other; and $Y^2$, $Y^3$, and $Y^4$ are any one of an alkyl group, an alkyl group having a fluorinated terminal, an aryl group, and one selected from the group consisting of an oligoalkylene ether group, an oligoalkylene thioether group, and an oligoalkylene amino group and including an electron donating group on carbon that is located in one of α-γ positions with respect to oxygen atom adjacent to M.

Further, a method of the present invention is a method for producing the ionic compound in which $Y^1$ is —$H(CH_3)CH_2(OCH_2CH_2)_{n-1}OCH_3$ group (where n is an integer equal to or more than 2). The method includes the step of reacting $AMH_4$ and 1,2-epoxy ethane having —$CH_2(OCH_2CH_2)_{n-1}OCH_3$ group in 1-position so as to synthesize $AMH_3OCH(CH_3)CH_2(OCH_2CH_2)_{n-1}OCH_3$.

According to the ionic compound of the present invention, characteristics (such as the ionic conductance) of the ionic compound can be improved while shortening a length of the oligoether group. The present inventors consider that such an advantage is achieved for following reasons. In the ionic compound of the present invention, the electron donating group is introduced in the vicinity of the central element M of the ate complex (anion). Therefore, an electron density around the central element M may increase so as to strengthen an ionic bond force between the ate complex and a cation $A^+$ of the group 1 element and an intermolecular interaction between molecules of the ionic compound. Here, the ion conduction of $A^+$ may be caused by a thermal agitation of the oligoalkylene group, the oligoalkylene thioether group or the oligoalkylene amino group (hereinafter referred to as "oligoether group") in a state that $A^+$ coordinates with a heteroatom (oxygen atom, sulfur atom or nitrogen atom) included in the oligoether group. Thus, $A^+$ of a certain molecule tends to move by the thermal agitation of the heteroatom of the oligoether group in a molecule adjacent to the certain molecule when the intermolecular interaction between molecules of the ionic compound becomes strong, so that the ionic conductance may be improved. Further, in the ionic compound of the present invention, the ionic bond force between the ate complex and the $A^+$ becomes strong as described above, but a steric hindrance of the electron donating group interferes with an approach of the A⁺ to the central element M of the ate complex. Thus, a dissociation between the central element M of the ate complex and A⁺, and the conduction of A⁺ may not deteriorate in the ionic compound of the present invention.

BEST MODES OF CARRYING OUT THE INVENTION

Figure 1:
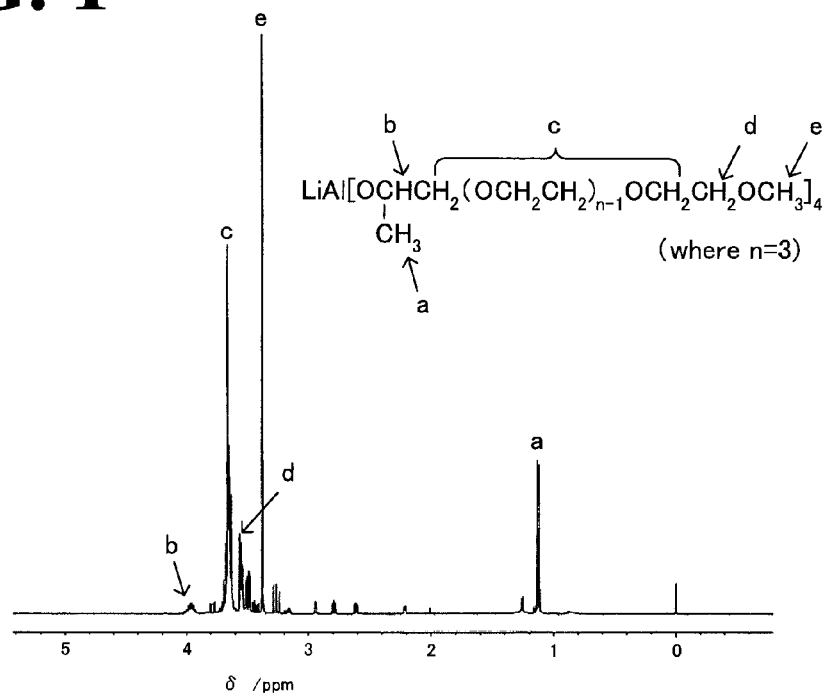
FIG. 1 is spectrum data of $^1$HNMR of Example 1.

The ionic compound of the present invention is the one represented by the above general formula (1): $AM(OY^1)(OY^2)(OY^3)(OY^4)$.

Here, A is a group 1 element. Preferably, A is Li or Na, more preferably Li.

M is a group 13 element. Preferably, M is B or Al.

$Y^1$ is an oligoether group including an electron donating group on carbon that is located in one of α-γ positions with respect to oxygen atom adjacent to M. Examples of the oligoether group include an oligoalkylene ether group, an oligoalkylene thioether group, and an oligoalkylene amino group. The oligoalkylene ether group has 2-20 alkylene oxide repeat units bonded together, where plurality of alkylene oxides of one or more kinds may be bonded together. The same structure can be applied to the oligoalkylene thioether group and the oligoalkylene amino group. Examples of the oligoalkylene ether group include oligoethylene ether group, oligopropylene ether group, and the like. Examples of oligoalkylene thioether group include an oligoethylene thioether group, an oligopropylene thioether group, and the like. Examples of the oligoalkylene amino group include an oligoethylene amino group, an oligopropylene amino group, and the like. A terminal structure of the oligoether group may be a structure in which an alkyl group, an aryl group or an alkyl-aryl group is bonded to a terminal heteroatom. Examples of the alkyl group include methyl, ethyl, propyl, isopropyl, n-butyl, isobutyl, sec-butyl, tert-butyl, and the like. Examples of the aryl group include phenyl, toluoyl, naphthyl, and the like. Examples of the alkyl-aryl group include benzyl and the like. Examples of the electron donating group included in the oligoether group include an alkyl group, an alkoxy group, an alkyl-amino group, and the like. Preferably, the electron donating group is the alkyl group. The alkyl group may be any one of groups mentioned above. Examples of the alkoxy group include methoxy, ethoxy, propoxy, isopropoxy, n-butoxy, isobutoxy, sec-butoxy, tert-butoxy, and the like. Examples of the alkyl-amino group include methylamino, dimethylamino, ethylamino, diethylamino, ethylmethylamino, and the like.

$Y^2$, $Y^3$, and $Y^4$ may be the same each other or different from each other or cross-linked to each other. $Y^2$, $Y^3$, and $Y^4$ are each any one of an alkyl group, an alkyl group having a fluorinated terminal, an aryl group, and one selected from the group consisting of an oligoalkylene ether group, an oligoalkylene a thioether group, and an oligoalkylene amino group, each of which includes an electron donating group on carbon that is located in one of α-γ positions with respect to oxygen atom adjacent to M. Examples other than the alkyl group having the fluorinated terminal are mentioned above. Examples of the alkyl group having the fluorinated terminal include trifluoromethyl, trifluoroethyl, hexafluoro-isopropyl, and the like. $Y^2$, $Y^3$, and $Y^4$ may be the same as $Y^1$.

Preferably, $Y^1$, $Y^2$, $Y^3$, and $Y^4$ are oligoalkylene ether groups and at least one of $Y^1$, $Y^2$, $Y^3$, and $Y^4$ includes the electron donating group on the carbon that is located in a position with respect to the oxygen atom adjacent to M and has 2-5 repeating numbers of the alkylene oxide. Thus, the repeating number is relatively small and the ratio of the alkylene oxide to A is small, so that an ionic density of A or a carrier ion increases.

An aprotic Lewis acid may be added to the ionic compound so as to provide an ion conductive material. Examples of the Lewis acid include $AlCl_3$, $FeCl_3$, $BF_3$, $TiCl_4$, and the like. However, the Lewis acid is not limited to these examples.

A salt including A of the formula (1) may be added to the ionic compound of the present invention so as to provide an ion conductive material. Examples of the salt including A is not specifically limited but, when A is Li, may be $LiPF_6$, $LiClO_4$, $LiBF_4$, $Li(CF_3SO_3)(LiTf)$, $Li(CF_3SO_2)_2N$ and the like.

The ionic compound of the present invention may be dispersed in the structural material so as to provide the ion conductive material. Examples of the structural material include polyethylene oxide (PEO), ethylene oxide-propylene oxide copolymer (EO-PO), poly(methoxyoligoethylene glycoxy)methacrylate, polymethyl methacrylate (PMMA), polyethyl methacrylate, polybutyl methacrylate, polyvinylidene difluoride (PVdF), vinylidene difluoride-hexafluoropropylene copolymer (PVdF-HFP), and the like. These compounds are excellent in the ionic conductance and film formability and suitable for a solid-electrolyte for lithium ion rechargeable battery, for example. Thus, the structural material may be any one of these compounds or a mixture of two or more of these compounds.

The ionic compound of the present invention may be obtained through a reaction caused by adding one equivalent weight of $Y^1OH$, one equivalent weight of $Y^2OH$, one equivalent weight of $Y^3OH$ and one equivalent weight of $Y^4OH$ to $AMH_4$ in a reaction solvent. Examples of $AMH_4$ include $LiAlH_4$, $LiBH_4$, and the like. Examples of the reaction solvent include ether solvents such as tetrahedrofuran (THF), diethylether, dimethoxyethane, and diglyme. The reaction temperature may be set in accordance with raw materials to be used, or in a range from −80° C. to 80° C., for example.

A method for producing the ionic compound in which $Y^1$ of the ionic compound is —$CH(CH_3)CH_2(OCH_2CH_2)_{n-1}OCH_3$ group (where n is an integer equal to or more than 2) may include the step of: reacting $AMH_4$ and 1,2-epoxy ethane having —$CH_2(OCH_2CH_2)_{n-1}OCH_3$ group in 1-position so as to synthesize $AMH_3OCH(CH_3)CH_2(OCH_2CH_2)_{n-1}OCH_3$. A reaction solvent may be used in the step. Examples of the reaction solvent include the above mentioned ether solvents. The reaction temperature may be set in accordance with raw materials to be used, or in a range from −80° C. to 80° C., for example. When oxygen atom of 1,2-epoxy ethane coordinates with M of $AMH_4$, the bond of the oxygen atom with the 1-position carbon or 2-position carbon may be cleaved. In the above step, the latter selectively occurs and the oxygen coordinates with M of $AMH_4$, so that $AMH_3[OCH(CH_3)CH_2(OCH_2CH_2)_{n-1}OCH_3]$ is selectively produced. By adjusting an amount of 1,2-epoxy ethane with respect to $AMH_4$, $AMH_{4-m}[OCH(CH_3)CH_2(OCH_2CH_2)_{n-1}OCH_3]_m$ (where m is an integer of from 1 to 4 and n is an integer equal to or more than 2) can be produced. The amount of 1,2-epoxy ethane may be equal to or slightly more than stoichiometry.

The ionic compound of the present invention may be a solid or a liquid. Preferably, the ionic compound is a liquid in terms of ionic conductance. The ionic compound of the present invention may be used as constituent materials of a capacitor, a lithium ion battery, a fuel cell, a solar cell and the like, reaction solvents for an organic reaction or an inorganic reaction, lubricants taking advantage of frictional characteristics, gas absorbents taking advantage of physical absorption characteristics, heating media taking advantage of thermal properties, and the like. When A or an alkali metal is Li, the ionic compound is preferably used as an electrolytic solution of the lithium ion secondary battery because the ionic compound of the present invention is nonvolatile and flame-retardant and has no fear of ignition.

EXAMPLES

Example 1

(1) Synthesis of PEG Having Glycidyl Group

PEG having a glycidyl group (1,2-epoxy ethane having PEG in 1-position) was synthesized according to following reaction formula where n=3 in this example. Concrete processes are described as follows.

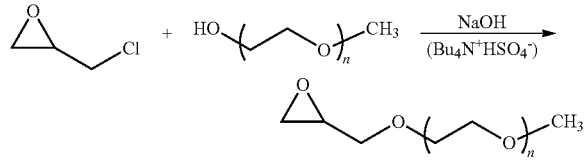

First, 12.49 g of large excess of epichlorohydrin, 2.29 g of 5 mol % phase transfer catalyst ($Bu_4N^+HSO_4^-$) and 5.4 g of 50 wt % NaOH aqueous solution were put into a 100 mL eggplant flask equipped with a dropping funnel and a condenser. While cooling the flask by immersion in an ice water bath, the mixture was stirred by a magnetic stirrer and then 7.39 g of polyoxyethylene monomethyl ether n=3 (hereinafter referred to as "PEG(3)M") was added to the contents of the flask by dropping for an hour. Further, the mixture was stirred for 15 hours for reaction. Subsequently, 50 mL of $CHCl_3$ was added to the resulting reaction mixture, that was a pale yellow colored emulsion, and then they were mixed. The mixed reaction mixture was extracted 4 times with water and once with brine and then dried with $Na_2SO_4$. The phase transfer catalyst was almost removed by these extraction treatments, but small amount of the phase transfer catalyst remained. The organic layer was heated up to 180° C. under a reduced pressure (200 Pa) produced by a vacuum pump for pyrolysis of the remaining phase transfer catalyst so as to obtain the distillation. The mother liquid residue was disposed. The distillation was heated up to 100° C. under the reduced pressure (200 Pa) produced by a vacuum pump so as to remove the pyrolysis component therein and small amount of unreacted PEG(3)M (b.p.=249° C.). Thus, 5.7 g (yield 580) of a colorless and transparent liquid was obtained. IR measurement and $^1H$, $^{13}C$-NMR measurements in $CDCl_3$ were performed for the colorless and transparent liquid. From the spectrum data, the resulting colorless and transparent liquid was identified as polyoxyethylene methyl glycidyl ether of n=3 (hereinafter referred to as Gly-PEG(3)M).

(2) Synthesis of Ionic Compound

An ionic compound was synthesized through a reaction between $LiAlH_4$ and polyoxyethylene methyl glycidyl ether according to following reaction formula. Concrete processes are described as follows.

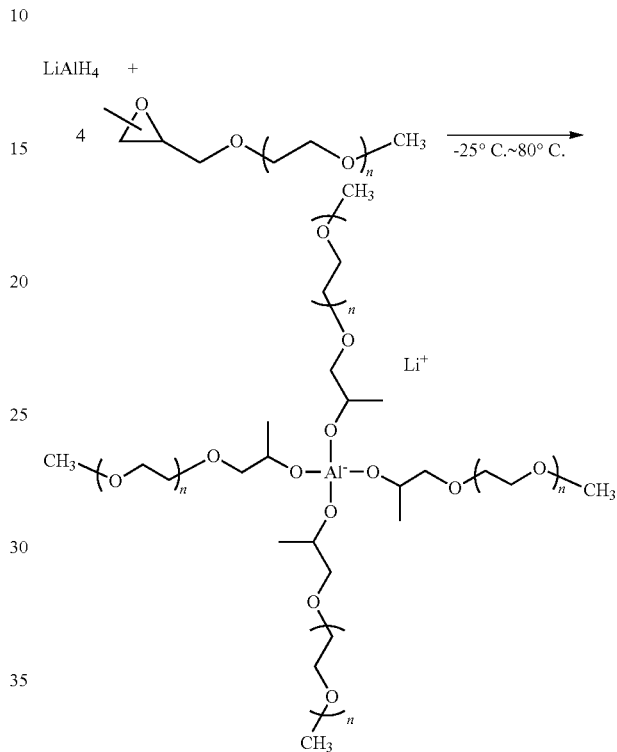

Figure 2:
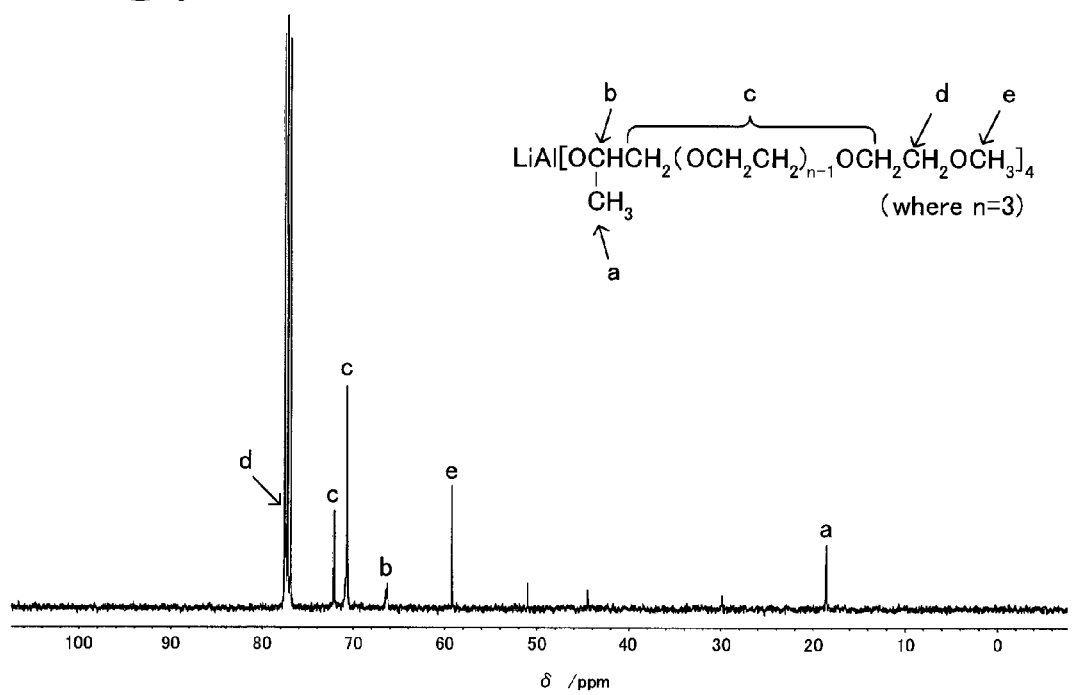
FIG. 2 is spectrum data of $^{13}$CNMR of Example 1.

Within an argon-filled glove box, 2.0 g of Gly-PEG(3)M was put in a sample bottle and dissolved in 5 mL of THF. Further, 2.3 mL of $LiAlH_4$ (1M THF solution) was introduced in a 50 mL eggplant flask. The eggplant flask was sealed with a rubber septum and immersed in a low-temperature bath kept at −25° C. The THF solution of the above Gly-PEG(3)M was introduced in a syringe and added to the contents of the eggplant flask for 10 minutes by dropping under a nitrogen gas stream. The reaction mixture was stirred for an hour at −25° C. and then stirred for 3 hours at a room temperature and for 15 hours at 45° C. for reaction. Then, the reaction mixture was heated up to 45° C. and distilled for an hour under a reduced pressure produced using an aspirator. The reaction mixture was decompressed down to about 270 Pa at the temperature and stirred for an hour. Further, the reaction mixture was heated up to 80° C. and stirred for 2.5 hours for a vacuum distillation, thereby obtaining $LiAl[OCH(CH_3)CH_2(OCH_2CH_2)_nOCH_3]_4$ (n=3) as an ionic compound, that was pale brown colored and transparent gel. The repeating number of the alkylene oxide of the compound was 4. $^1H$, $^{13}C$-NMR spectra in $CDCl_3$ were measured for the compound. The spectrum data are shown in FIGS. 1 and 2. The above reaction did not generate hydrogen gas and generated less heat in comparison with a reaction using alcohol instead of Gly-PEG(3)M.

(3) Measurement of Ionic Conductance

Figure 3:
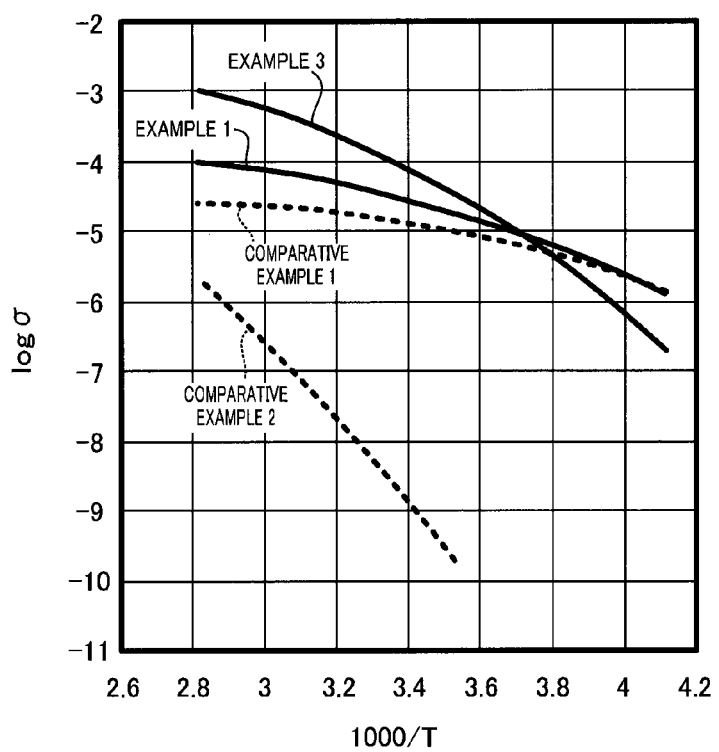
FIG. 3 is a graph indicating ionic conductance characteristics of Examples 1, 3 and Comparative Examples 1, 2.

Within an argon-filled glove box, Gly-PEG(3)M was put into an inside of a measurement cell (diameter φ=10 m) and an air bubble was bled off from the Gly-PEG(3)M so as to seal the cell. After measuring a film thickness, the measurement cell was placed in a constant temperature bath and temperature was set at 25° C., 10° C., −10° C., −30° C., −10° C., 10° C., 25° C., 45° C., 60° C., 70° C., 80° C., 80° C., 70° C., 60° C., 45° C., and 25° C. An impedance measurement was performed after holding each temperature for 2 hours. The impedance measurement was performed at an amplitude voltage of 300 mV and 0.5 pts/sec in the range from 1 MHz to 0.1 Hz. Then, a value of Z' real-axis intercept of the resulting Cole-Cole plot or |Z| minimizing θ in the Bode plot was obtained as a resistance value (R). An ionic conductance σ (Scm$^{-1}$) was calculated based on the resistance value (R), the film thickness t (cm) and an electrode surface area according to following equation. The result is shown in FIG. 3. T of the lateral axis in FIG. 3 is in the unit of kelvin (K).

$$\sigma = 1/R \times t/S$$

Example 2

(1) Synthesis of PEG Having Glycidyl Group

Polyoxyethylene methyl glycidyl ether of n=11.8 was synthesized through similar processes as (1) in Example 1. In this case, the filtrate was extracted 4 times with water and once with brine and then dried with $Na_2SO_4$. Then, the organic layer was evaporated in an evaporator and heated up to 180° C. under the reduced pressure (200 Pa) using a vacuum pump for distillation. The phase transfer catalyst remaining after the extraction was pyrolyzed by the heat upon the distillation. Then, the residue was dissolved into chloroform and extracted with water and brine. The extract was dried with $Na_2SO_4$ and heated up to 100° C. under the reduced pressure (200 Pa) using a vacuum pump for distillation so as to sufficiently remove the decomposition product of the phase transfer catalyst. Thus, a colorless and transparent liquid of 11.9 g (yield 59%) was obtained. $^1$H, $^{13}$C-NMR spectra were measured for the colorless and transparent liquid. From the spectrum data, the resulting colorless and transparent liquid was identified as Polyoxyethylene methyl glycidyl ether of n=11.8 (hereinafter referred to as Gly-PEG(11.8)M).

(2) Synthesis of Ionic Compound

Figure 4:
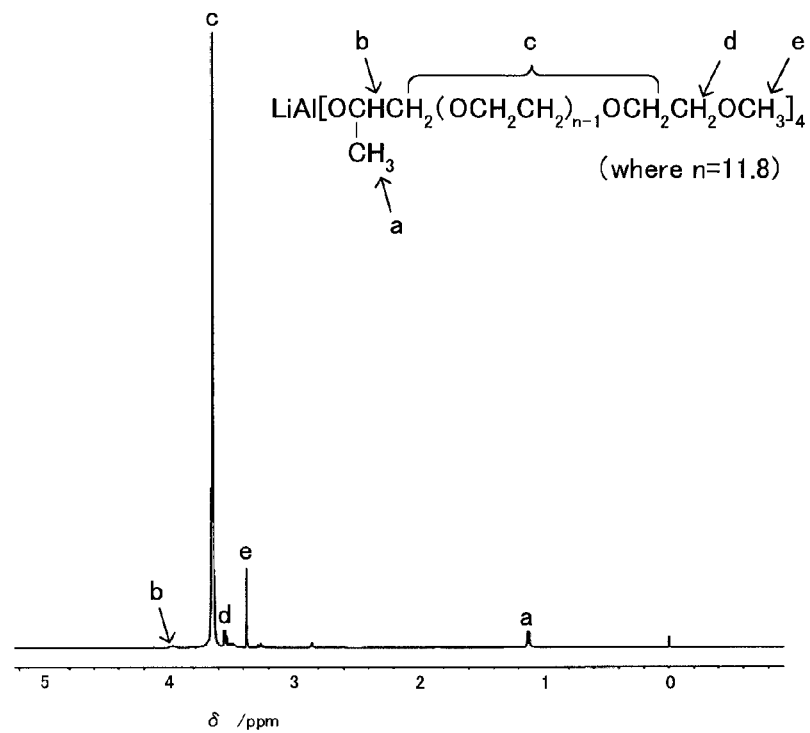
FIG. 4 is spectrum data of $^1$HNMR of Example 2.
Figure 5:
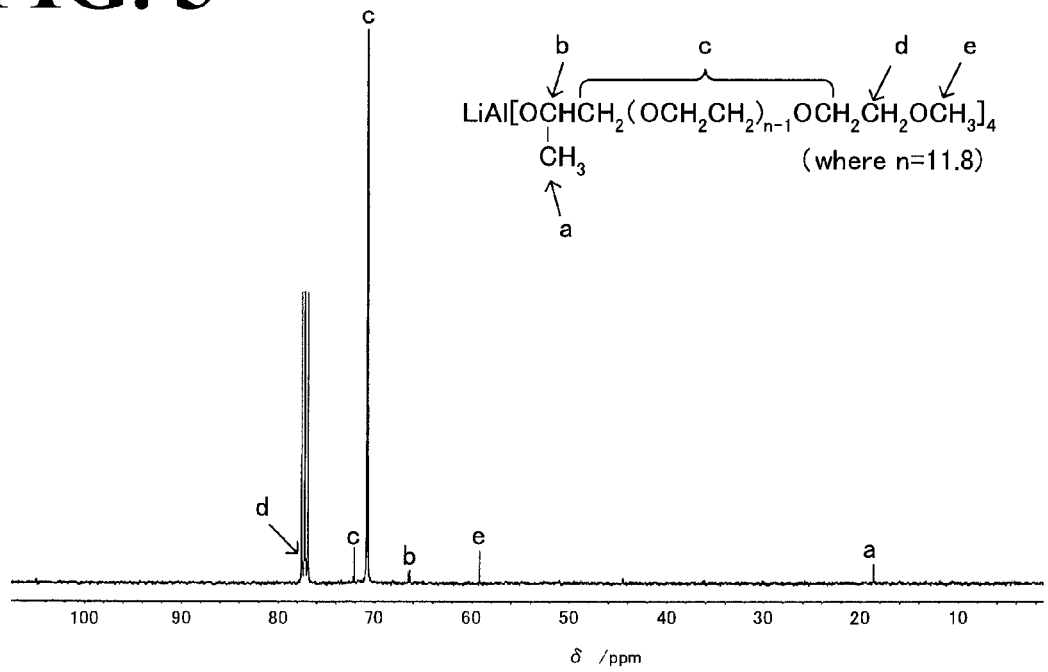
FIG. 5 is spectrum data of $^{13}$CNMR of Example 2.

LiAl[OCH($CH_3$)$CH_2$(O$CH_2CH_2$)$_n$O$CH_3$]$_4$ (n=11.8) as an ionic compound, that was a pale yellow colored and transparent liquid, was obtained using Gly-PEG(11.8)M instead of Gly-PEG(3)M of (2) in Example 1. The repeating number of the alkylene oxide of the compound was 12.8. $^1$H, $^{13}$C-NMR spectra in $CDCl_3$ were measured for the compound. The spectrum data are shown in FIGS. 4 and 5.

(3) Measurement of Ionic Conductance

The ionic conductance of the ionic compound (n=11.8) was measured through similar processes as (3) in Example 1. Here, an ion conductive material was prepared so that EO (ethylene oxide):Li becomes 14:1 by adding LiTf to the ionic compound and the ionic conductance of the ion conductive material was measured. The resulting log σ was $1 \times 10^{-4}$ to $1 \times 10^{-3}$ at 25° C. (1000/T=3.4).

Example 3

Within the argon-filled glove box, 0.6 g of the jelly gel ionic compound (n=3) of Example 1 and 87 mg of anhydrous aluminum chloride ($AlCl_3$) were introduced in the 50 mL eggplant flask and 5 mL of THF was added to the contents of the eggplant flask. The reaction mixture was stirred under a nitrogen gas stream for a night at room temperature. Then, the reaction mixture was heated up to 45° C. in a hot water bath and stirred for 3 hours. Further, the reaction mixture was gradually heated up to 60° C. and the solvent was evaporated under a reduced pressure, thereby obtaining an ion conductive material that was an amber colored and transparent homogeneous jelly gel. This ion conductive material was obtained by adding $AlCl_3$ as Lewis acid to the ionic compound (n=3) of Example 1. The ionic conductance of this ion conductive material was measured through similar processes of (3) in Example 1. The result is shown in FIG. 3.

Comparative Example 1

LiAl[O$CH_2CH_2$(O$CH_2CH_2$)$_{n-1}$O$CH_3$]$_4$ (n=3) as an ionic compound was synthesized according to literature of Shigehara et al. (Chem. Mater., 1996, vol. 8, p 469-472). The ionic conductance of this ionic compound was measured through similar processes of (3) in Example 1. The result is shown in FIG. 3.

Comparative Example 2

LiAl[OCH($CH_3$)$CH_2$(O$CH_2CH_2$)$_n$O$CH_3$]$_4$ (n=0) as an ionic compound was synthesized as in the case of Example 1. The ionic conductance of this ionic compound was measured through similar processes of (3) in Example 1. The result is shown in FIG. 3.

Discussion

As seen from FIG. 3, the ionic conductance of the ionic compound (n=3) of Example 1 was larger than that of the ionic compound of the Comparative Example 1 throughout the range from −30° C. to 80° C. (2.8-4.1 in 1000/T). Further, the rate of change of the ionic conductance with respect to temperature of the ionic compound of Example 1 was substantially equal to Comparative Example 1 and small. Thus, the ionic compound of Example 1 may improve battery characteristics because of its large ionic conductance when it is used as an electrolyte solution of the lithium ion secondary battery. Further, the ionic compound of Example 1 may stabilize an output of battery because of its small rate of change of the ionic conductance with respect to temperature.

The ionic conductance of the ion conductive material of Example 3 was larger than that of the ionic compound of Example 1 at 0° C. to −80° C. (2.8-3.7 in 1000/T) and smaller than that of the ionic compound of Example 1 at −30° C. to −0° C. (3.7-4.1 in 1000/T). The result was generally favorable. The rate of change of the ionic conductance with respect to temperature of the ionic compound of Example 3 was slightly larger than that of Example 1. Thus, the ionic compound of Example 3 may also improve battery characteristics when it is used as an electrolyte solution of the lithium ion secondary battery and stabilize the output of battery as the ionic compound of Example 1.

On the other hand, the ionic conductance of the ionic compound of the Comparative Example 2 was smaller by an order of magnitude or more than that of the Comparative Example 1 at 10° C. to 80° C. (2.8-3.5 in 1000/T, ionic conductance at below 10° C. was not measured). Further, the rate of change of the ionic conductance with respect to temperature of the Comparative Example 2 was outstandingly larger than that of the Comparative Example 1. The reasons remain unclear but may be as follows. That is, in the ionic compound of n=0, an ion conduction of Li$^+$ is not caused by a thermal agitation of the oxygen atom of the oligoether group in the molecule due to shortage of the ethylene oxide, so that the ionic conductance and the rate of change of the ionic conductance may deteriorate.

Regarding to the ionic compound (n=11.8) of Example 2, the ionic conductance of the ion conductive material obtained by adding LiTf to the ionic compound was measured as described above (shown in FIG. 6). The rate of change of the ionic conductance with respect to temperature of the ionic conductive material of Example 2 was larger than that of the Example 1. The reasons remain unclear but may be as follows. That is, in the case of n=1-4 (repeating number of alkylene oxide is 2-5), when the intermolecular interaction between molecules of the ionic compound becomes strong, $A^+$ of a certain molecule tends to move by the thermal agitation of the heteroatom of the oligoether group in a molecule adjacent to the certain molecule. As a result, the ionic conductance may be improved and the rate of change of the ionic conductance with respect to temperature may be stabilized. On the contrary, in the case where n is larger than 4 (repeating number of alkylene oxide becomes larger than 5), $A^+$ of the certain molecule tends to move by not the thermal agitation of the heteroatom of the oligoether group in the molecule adjacent to the certain molecule but by the thermal agitation of the heteroatom of the oligoether group in the certain molecule. Accordingly, the ionic conductance may not be sufficiently improved though the intermolecular interaction between molecules of the ionic compound becomes strong.

Example 4

Figure 6:
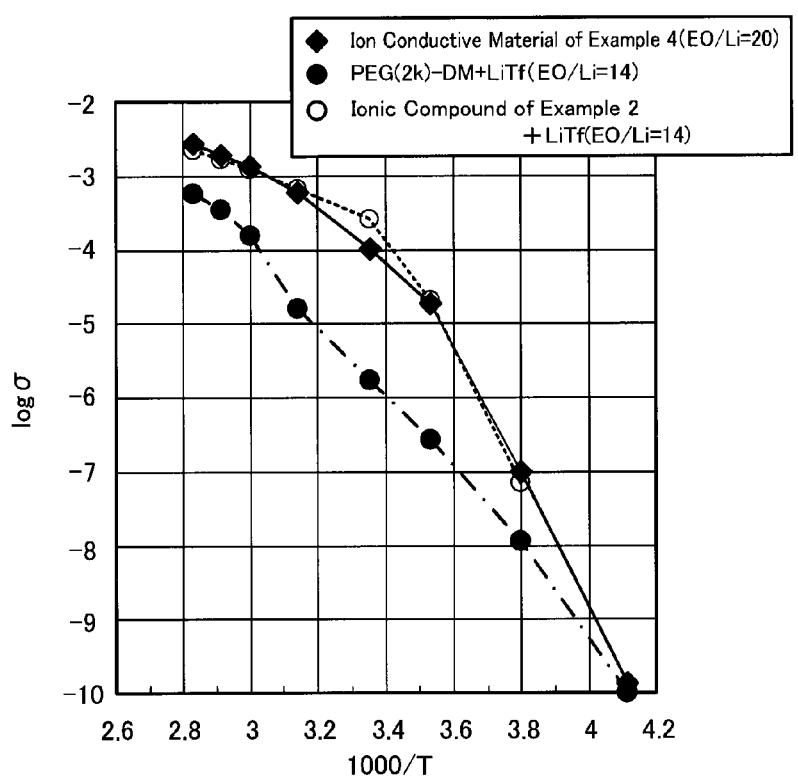
FIG. 6 is a graph indicating ionic conductance characteristics of Examples 4 and other examples.

An Ion conductive material (composite electrolyte) was synthesized according to the reaction formula described below. Concretely, within a glove box (Argon), 85 mg of PEG (2 k)-DM and 0.20 g of the ionic compound (n=11.8) of Example 2 were put in a dried 20 mL sample bottle. Then, 2.2 mL of 0.1M acetonitrile solution of LiTf was introduced in the sample bottle and the sample bottle was sealed. The mixture was homogeneously dispersed and dissolved by an ultrasonic dispersion and evaporated under a reduced pressure. Thus, a solid ion conductive material was obtained. In this case, the ionic compound of Example 2 and the mixture of the ionic compound and LiTf were liquid and the ionic conductive material obtained in Example 4 was a waxy free standing film. The result of a conductance measurement is shown in FIG. 6. As shown in FIG. 6, the ionic conductance of the ion conductive material of Example 4 was not very different from that of the ionic compound to which PEG(2 k)-DM was not added.

Example 4

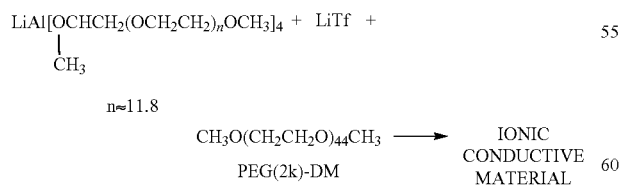

Example 5

Figure 7:
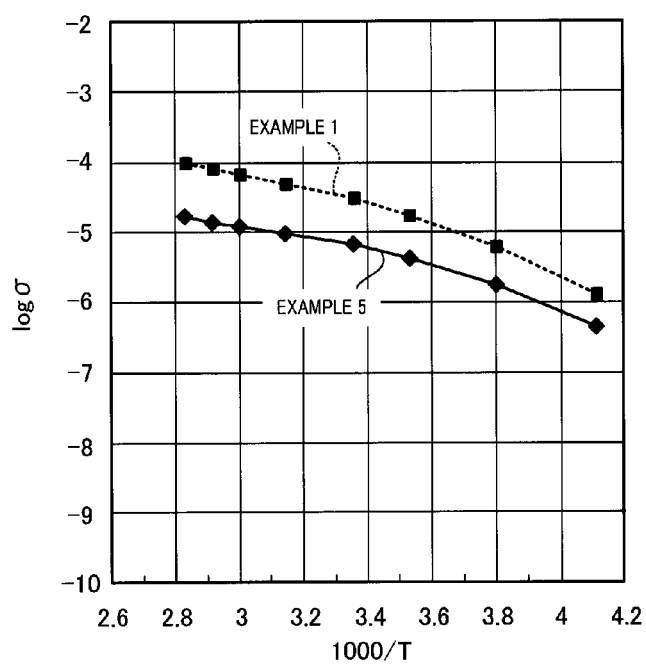
FIG. 7 is a graph indicating ionic conductance characteristics of Examples 1 and 5.
Figure 8:
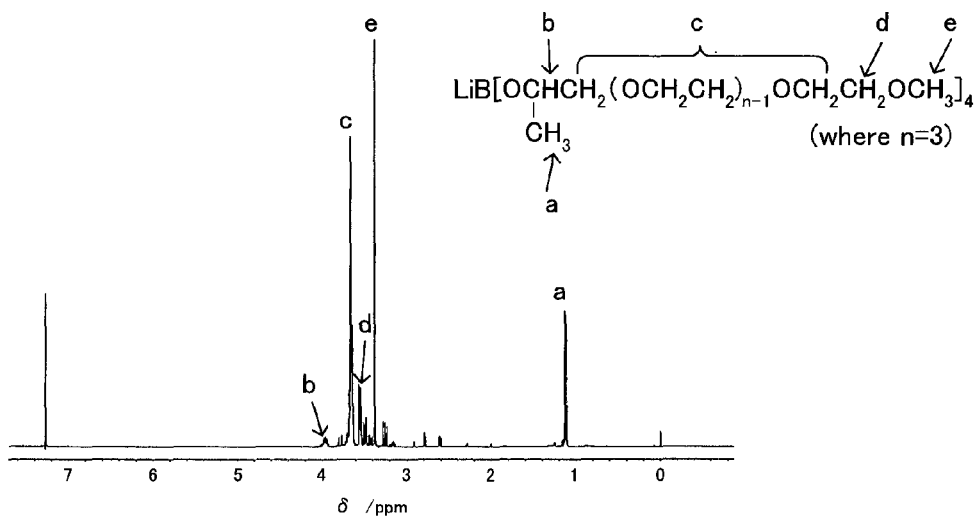
FIG. 8 is spectrum data of $^1$HNMR of Example 5.
Figure 9:
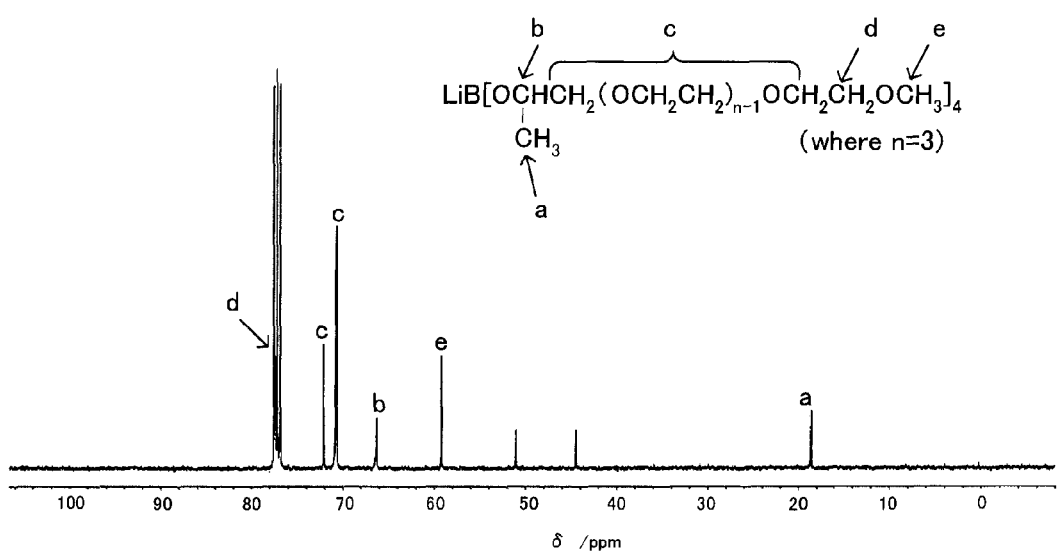
FIG. 9 is spectrum data of $^{13}$CNMR of Example 5.

An Ionic compound was synthesized using B instead of Al of Example 1 according to the reaction formula described below. Concretely, within an argon-filled glove box, 2.0 g of Gly-PEG(3)M was put in a sample bottle and dissolved into 5 mL of THF. Further, 1.14 mL of LiBH$_4$ (2M THF solution) was put in a 50 mL eggplant flask. The eggplant flask was sealed with a rubber septum and immersed in the low-temperature bath kept at −25° C. The Gly-PEG(3)M solution was introduced in a syringe and added to the contents of the eggplant flask for 25 minutes by dropping under the nitrogen gas stream. The reaction mixture was stirred for an hour at the temperature and then stirred for 19 hours at room temperature for reaction. Then, the reaction mixture was heated up to 55° C. and decompressed up to about 210 Pa by a vacuum pump for 10 hours, thereby obtaining a transparent gel product. The result of a conductance measurement is shown in FIG. 7. As shown in FIG. 7, the ionic conductance σ of the ionic compound of Example 5 was slightly smaller than that of the ionic compound of Example 1 but large enough. $^1$H, $^{13}$C-NMR spectra in CDCl$_3$ were measured for the ionic compound of Example 5. The spectrum data are shown in FIGS. 8 and 9.

Example 5

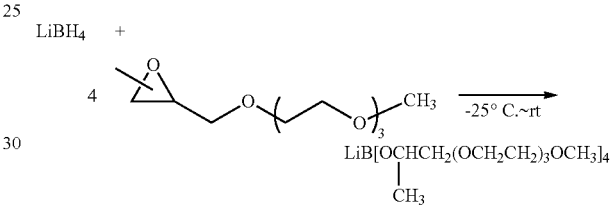

The present application claims priority from the Japanese Patent Application No. 2010-212245 filed on Sep. 22, 2010, the entire contents of which are incorporated herein by reference.

INDUSTRIAL APPLICABILITY

The ionic compound of the present invention can be applied to an antistatic agent, an electrolytic solution, a high temperature catalyst, a lubricant, a solvent to dissolve sugar, and the like, in particular to the electrolytic solution of the lithium ion secondary battery.

The invention claimed is:
1. An ionic compound that is represented by the formula (1):

AM(OY$^1$)(OY$^2$)(OY$^3$)(OY$^4$), wherein A is a group 1 element;
M is a group 13 element;
Y$^1$ is one selected from the group consisting of
an oligoalkylene ether group that includes an electron donating group on carbon that is located in one of α-γ positions with respect to oxygen atom adjacent to M, wherein the oligoalkylene ether group has 2 to 20 alkylene oxide repeat units bonded together,
an oligoalkylene thioether group that includes an electron donating group on carbon that is located in one of α-γ positions with respect to oxygen atom adjacent to M, and
an oligoalkylene amino group that includes an electron donating group on carbon that is located in one of α-γ positions with respect to oxygen atom adjacent to M;

$Y^2$, $Y^3$, and $Y^4$ are the same each other or different from each other or cross-linked to each other; and $Y^2$, $Y^3$, and $Y^4$ are each selected from the group consisting of an oligoalkylene ether group that includes an electron donating group on carbon that is located in one of α-γ positions with respect to oxygen atom adjacent to M, an oligoalkylene thioether group that includes an electron donating group on carbon that is located in one of α-γ positions with respect to oxygen atom adjacent to M, and an oligoalkylene amino group that includes an electron donating group on carbon that is located in one of α-γ positions with respect to oxygen atom adjacent to M.

2. The ionic compound according to claim 1, wherein A is Li or Na and M is Al or B.

3. The ionic compound according to claim 1, wherein $Y^1$, $Y^2$, $Y^3$, and $Y^4$ are the oligoalkylene ether group; and at least one of $Y^1$, $Y^2$, $Y^3$, and $Y^4$ includes the electron donating group on carbon that is located in a position with respect to oxygen atom adjacent to M and has 2-5 repeating numbers of the alkylene oxide.

4. The ionic compound according to claim 1, wherein the electron donating group is alkyl group.

5. An ion conductive material comprising the ionic compound according to claim 1, wherein an aprotonic Lewis acid is added to the ionic compound.

6. An ion conductive material comprising the ionic compound according to claim 1, wherein a salt including A of the formula (1) is added to the ionic compound.

7. An ion conductive material comprising a structural material and the ionic compound according to claim 1, wherein the ionic compound is dispersed in the structural material.

8. A method for producing the ionic compound according to claim 1, $Y^1$ of the ionic compound being
—$CH(CH_3)CH_2(OCH_2CH_2)_{n-1}OCH_3$ group, where n is an integer of 2 to 20, the method comprising the step of:
reacting $AMH_4$ and 1,2-epoxy ethane having —$CH_2(OCH_2CH_2)_{n-1}OCH_3$ group in 1-position so as to synthesize $AMH_3OCH(CH_3)CH_2(OCH_2CH_2)_{n-1}OCH_3$.

* * * * *